United States Patent [19]

Imran

[11] Patent Number: 4,796,620
[45] Date of Patent: Jan. 10, 1989

[54] SYSTEM FOR SENSING ABNORMAL HEART ACTIVITY BY MEANS OF HEART RATE ACCELERATION AND DECELERATION DETECTION

[75] Inventor: Mir Imran, San Francisco, Calif.

[73] Assignee: Mieczyslaw Mirowski, Owings Mills, Md.

[21] Appl. No.: 862,785

[22] Filed: May 13, 1986

[51] Int. Cl.$^4$ .............................................. A61B 5/04
[52] U.S. Cl. ................... 128/706; 128/419 D; 128/702
[58] Field of Search ...................... 128/702–706, 128/708, 419 D

[56] References Cited

U.S. PATENT DOCUMENTS

| | | | |
|---|---|---|---|
| 3,398,736 | 8/1968 | Brant et al. | 128/706 |
| 3,618,593 | 11/1971 | Nachev et al. | 128/702 |
| 3,699,949 | 10/1972 | O'Hanlon, Jr. et al. | 128/706 |
| 3,718,827 | 2/1973 | Ragsdale | 128/702 |
| 3,837,333 | 9/1974 | Bruckheim | 128/706 |
| 4,184,493 | 1/1980 | Langer et al. | 128/419 D |
| 4,202,340 | 5/1980 | Langer et al. | 128/419 D |
| 4,393,877 | 7/1983 | Imran et al. | 128/705 |
| 4,457,315 | 7/1984 | Bennisti | 128/704 |
| 4,614,192 | 9/1986 | Imran et al. | 128/419 D |

FOREIGN PATENT DOCUMENTS

| | | |
|---|---|---|
| 2331551 | 1/1974 | Fed. Rep. of Germany . |
| 2543713 | 4/1977 | Fed. Rep. of Germany . |
| 2750646 | 11/1977 | Fed. Rep. of Germany . |
| 2717747 | 12/1977 | Fed. Rep. of Germany . |
| 3031576 | 8/1980 | Fed. Rep. of Germany . |

Primary Examiner—William E. Kamm
Attorney, Agent, or Firm—Fleit, Jacobson, Cohn & Price

[57] ABSTRACT

A heart rate acceleration/deceleration detecting system particularly for use with an automatic defibrillator/cardioverter. The detection system detects a series of heart beats and determines, for a group of beats, such as on a beat-by-beat basis, whether the heart rate has accelerated above a first predetermined value. If such acceleration is determined, the system checks to see if the acceleration of the heart beats was followed by an immediate deceleration that exceeds a predetermined value. If a large acceleration followed by an absence of a large deceleration is detected, a signal is provided to an arrhythmia detecting logic circuit as an indication of an arrhythmia that may be appropriate for treatment by the defibrillator/cardioverter. The acceleration detection system is also capable of determining if a large deceleration preceded the detection of the large acceleration. If a large deceleration preceding a large acceleration had been detected, the system assumes that an AGC dropout in a rate detector circuit had occurred and will not provide an output signal to the arrhythmia detecting logic circuit. The system is also capable of detecting premature ventricular contractions by the existence of a large acceleration followed immediately by a large deceleration.

5 Claims, 3 Drawing Sheets

SYSTEM FOR SENSING ABNORMAL HEART ACTIVITY BY MEANS OF HEART RATE ACCELERATION AND DECELERATION DETECTION

BACKGROUND OF THE INVENTION

The present invention relates to a heart rate acceleration/deceleration detection system. The system has particular utility as part of an automatic implantable defibrillator (or cardioverter) that provides high-energy electrical pulses directly to the heart in response to the detection of a life-threatening arrhythmia.

In recent years, substantial progress has been made in the development of techniques for effectively defibrillating or cardioverting various heart disorders and arrhythmias. Past efforts have resulted in the development of implantable electronic standy defibrillators which, in response to the detection of an abnormal cardiac rhythm, discharge sufficient energy via electrodes connected to the heart to depolarize and restore it to normal cardiac rhythm.

Research efforts have also been directed toward developing techniques for reliably monitoring heart activity in order to determine whether defibrillation of cardioversion is necessary. Such techniques include monitoring the heart rate or determining the presence of fibrillation on the basis of a probability density function (PDF). A system using the PDF technique statistically evaluates the time the cardiac waveform spends away from the zero-potential axis. When the waveform becomes dangerously irregular, as measured by its probability density function, an abnormal cardiac function requiring defibrillation or cardioversion is suggested. This PDF technique is described in commonly owned U.S. Pat. Nos. 4,184,493 and 4,202,340, both of Langer et al.

Another system for monitoring heart activity utilizes both the PDF technique to determine the presence of an abnormal cardiac rhythm and a heart rate sensing circuit for indicating, with the PDF technique, ventricular fibrillation and high rate tachycardia (indicated by heart rate above a predetermined minimum threshold). Upon the detection of high rate tachycardia, i.e., upon the heart rate sensing circuit output exceeding a predetermined threshold, an arrhythmia condition is assumed and a defibrillating or cardioverting pulse is issued. A typical heart rate detection circuit is shown in commonly owned U.S. Pat. No. 4,393,877 to Imran et al. Another heart rate detecting circuit using an automatic gain control (AGC) feedback circuit is described in co-pending U.S. patent application Ser. No. 478,038 filed on Mar. 23, 1983 (a continuation of Ser. No. 370,191, filed on Apr. 21, 1982) to Imran et al, now U.S. Pat. No. 4,614,192.

As discussed in U.S. Pat. No. 4,393,877, a defibrillating pulse may be issued in response to outputs from both the PDF circuit and the heart rate averaging circuit or in response to the heart rate averaging circuit alone. That is, in certain circumstances it may be desirable to treat an arrhythmia solely in response to the average heart rate exceeding a predetermined threshold.

With some patients, however, the mere presence of an average heart rate above a predetermined threshold may not warrant the delivery of a defibrillating or cardioverting pulse. For example, certain patients, despite requiring a defibrillator implant, may still be able to engage in relatively strenuous exercise which could cause their heart rate to exceed the threshold level that would normally indicate an arrhythmia. For such patients, it is important to protect against the implanted device issuing an unnecessary and unwanted high energy pulse in response to such high heart rate.

It is thus seen that a need exists for an implantable defibrillator or cardioverter that is able to distinguish between high rate tachycardia that requires a corrective defibrillating or cardioverting shock and high rate normal sinus rhythm resulting from strenuous exercise or the like that does not warrant treatment.

SUMMARY OF THE INVENTION

The present invention recognizes that a detected high rate condition resulting from strenuous exercise or the like is typically reached gradually, whereas the heart rate in a tachycardia requiring corrective treatment rises relatively quickly. That is, if the heart rate accelerates slowly, such condition is deemed to result from normal exercise and does not require a defibrillating or cardioverting shock.

Thus, it is an object of the present invention to provide a system for detecting the magnitude of acceleration of the heart rate to determine if the heart rate has accelerated relatively quickly, thus indicating a treatable arrhythmic condition. Upon an indication of such rapid acceleration, along with an indication of high rate from the heart rate averaging circuit, a life-threatening arrhythmic condition is assumed, and a shock is issued.

The present invention further recognizes that a relatively high acceleration rate (on a beat-to-beat basis) may also occur in the presence of premature ventricular contractions (PVC), a condition which does not normally require countershock treatment. The presence of a PVC is typically characterized by a rapid acceleration of the beat-to-beat heart rate immediately followed by a rapid deceleration of the beat-to-beat heart rate. That is, a premature beat closely follows a prior beat (rapid acceleration) with the subsequent beat following in its "normal" beat position. If such acceleration and subsequent deceleration exceed predetermined values, a PVC condition is assumed and the arrhythmia detecting logic remains passive.

Still further, it is an object of the present invention to detect the existence of an excessive deceleration that immediately precedes the detection of an excessive acceleration and to prevent a defibrillating or cardioverting pulse upon such occurrences. Such condition is typically caused by automatic gain control (AGC) dropout of the heart rate detector. That is, the heart rate detector of the present invention preferably includes an AGC feedback path, as is described in U.S. Pat. No. 4,614,192. Because of the AGC circuit, a heartbeat, i.e., an R- wave, may be detected late resulting in "deceleration" of the heart rate. When the AGC resumes control, the normal heart rate would look like acceleration. Thus, an acceleration event which immediately follows deceleration is ignored by the circuit, and thus prevents unwanted triggering of the pulse generator.

These and other objects of the invention will be more clearly understood by reference to the following detailed description and the accompanying drawings.

DETAILED DESCRIPTION OF THE PREFERRED EMBODIMENT

Figure 1:
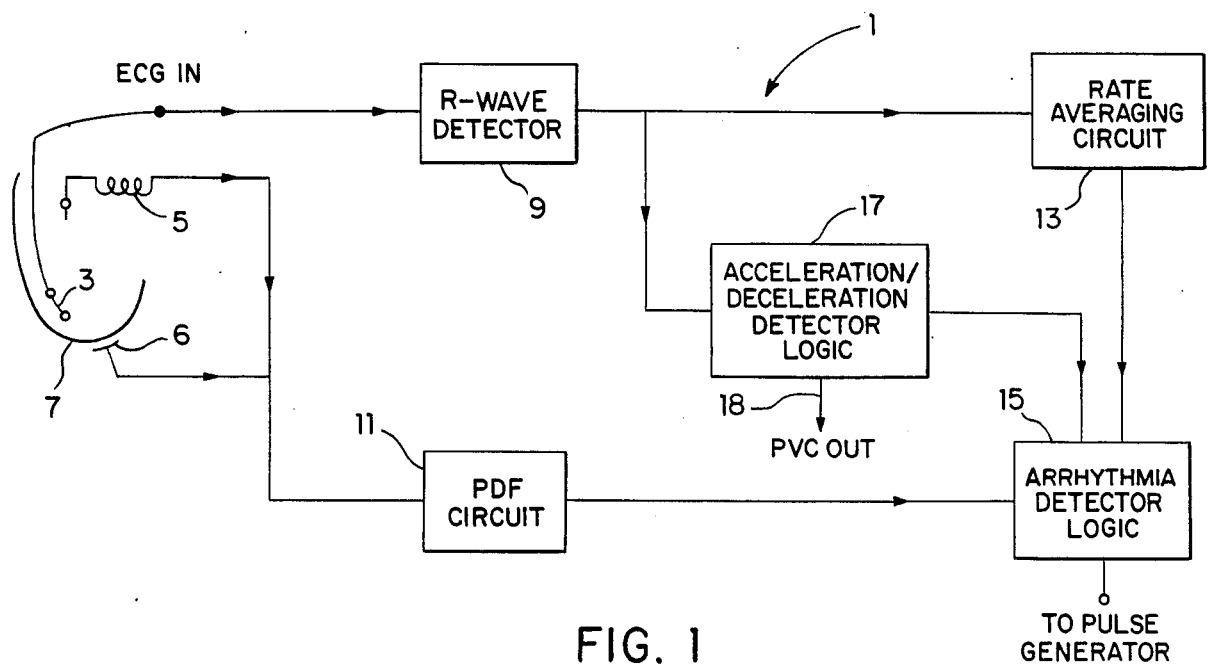
FIG. 1 is a block diagram of an arrhythmia detection system as part of an automatic implantable defibrillator/cardioverter.

The arrhythmia detecting system 1 of the present invention, is depicted schematically in FIG. 1. The arrhythmia detecting system 1 is adapted to be coupled with electrodes 3 and 5, which are connected to the heart 7 of the patient. The electrodes include a bipolar sensing electrode 3, adapted to be located in the right ventricle for ECG sensing of ventricular contractions, and intracardiac sensing and high voltage delivery electrode 5 adapted to be located in the superior vena cava (SVC) for delivering the high-voltage defibrillating-/cardioverting pulses. A patch electrode 6 is connected to the myocardium of the heart, 7, or an additional electrode surface can be placed near electrodes 3 and 5. The bipolar electrode 3 provides an ECG input signal to an R-wave detector circuit 9. The SVC electrode 5, acting with the patch electrode 6, provides the input to a PDF circuit 11.

The R-wave detector circuit 9 may be similar to that disclosed in U.S. Pat. No. 4,614,192 or that disclosed in U.S. Pat. No. 4,393,877. Basically, the R-wave detector circuit 9 detects the R-waves and provides uniform pulses proportional to the R-waves of the incoming ECG signal. The time between R-waves is inversely proportional to the rate of R-waves, or the heart rate.

The PDF circuit may be that described in U.S. Pat. Nos. 4,184,493 and 4,202,340.

The R-wave detector circuit 9 has its output coupled with a rate averaging circuit 13 which receives the detected R-waves, calculates the average heart rate, and provides an output when the average heart rate exceeds a predetermined value. The rate averaging circuit may be that disclosed in U.S. Pat. No. 4,393,877 or U.S. Pat. No. 4,614,192 (see elements 80 and 36 of FIG. 2 of the U.S. Pat. No. 4,614,192. The outputs of the rate averaging circuit 13 and the PDF circuit 11 are provided as inputs to an arrhythmia detector logic circuit 15. Such logic 15 may include an AND gate, the inputs of which receive the outputs of the rate averaging circuit 13 and the PDF circuit 11 so as to provide an output to a pulse-generator (not shown) upon the concurrence of output signals from the PDF circuit 11 and the rate averaging circuit 13, as is known in the art. Alternatively, and preferably, the detector logic 15 includes a means for disabling the PDF circuit 11 output when it is desired to detect an arryhthmia solely upon the basis of high average heart rate from 13. The logic to disable the PDF circuit 11, and to detect arrhythmias solely on the basis of the rate averaging circuit 13, is described in U.S. Pat. No. 4,393,877.

The novel heart rate acceleration/deceleration detecting system 17 of the present invention is depicted schematically in FIG. 1. The acceleration/deceleration detecting logic 17 is connected with the R-wave detector 9 to receive electrical pulses indicative of the heart rate. As set forth, these pulses are proportional to the R-waves that are detected from the ECG wave packet wherein the instanteous heart rate can be calculated, as is well-known in the art, by measuring the time interval between the detected R-waves. This time interval is inversely proportional to the instantaneous heart rate. Alternatively, the R-wave detector 9 may itself include circuitry for converting the detected R-waves into instantaneous readings of the heart rate, and provide such heart rate information, in digital form, to the acceleration/deceleration detecting system 17.

The acceleration/deceleration rate detecting system 17 receives the R-wave pulses and determines the heart rate on a beat-by-beat basis. The system 17 determines if the heart rate is accelerating excessively, and performs other logic in a manner to be described. If an acceleration is determined, of the type that may require a defibrillating/cardioverting pulse, the acceleration/deceleration detecting system 17 provides an output signal to the arrhythmia detector logic circuit 15. Upon the occurrence of an output from the rate averaging circuit 13 and the acceleration/deceleration detector circuit 17, the arrhythmia detector logic provides an output to the pulse generator. Such a logic may be a simple AND gate. Similarly, if the PDF circuit 11 is also to be monitored to determine an arrhythmia, then output signals from the PDF circuit 11, the rate averaging circuit 13 and the acceleration/deceleration detecting system 17 are required for the detector logic 15 to trigger the pulse generator. Each of these signals may comprise inputs to an AND gate, or other logic.

Figure 2:
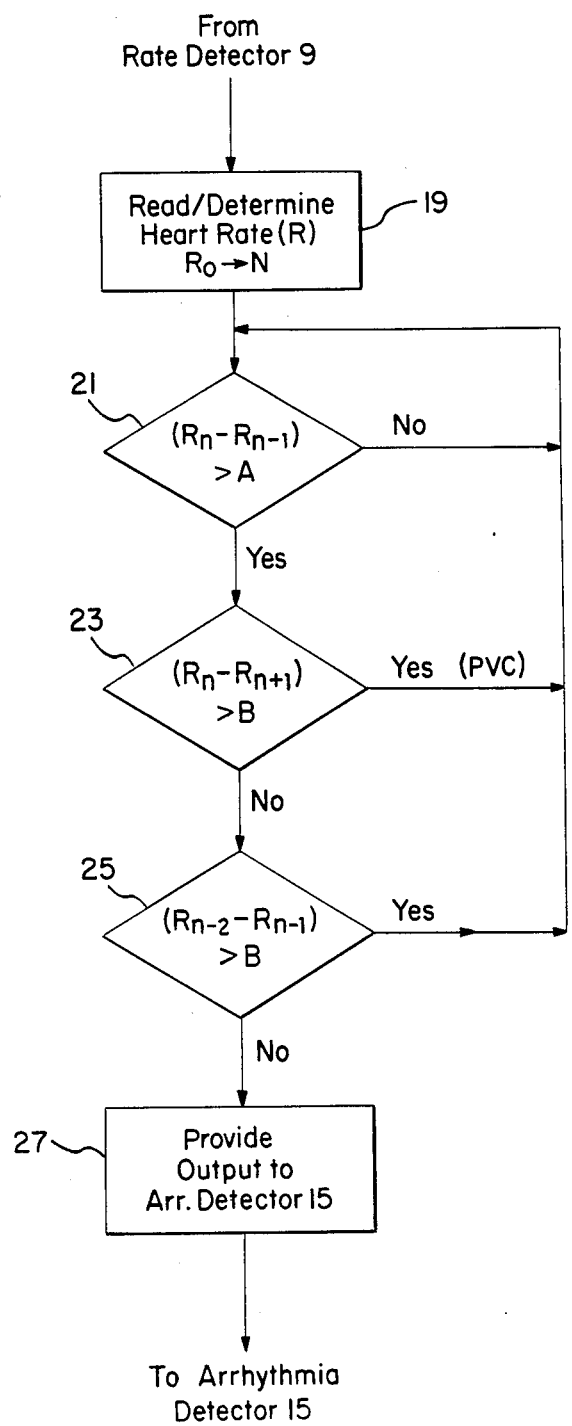
FIG. 2 is a schematic functional flow chart of the acceleration/deceleration detector logic of FIG. 1.

A functional flow chart of the acceleration/deceleration detecting operation is depicted in FIG. 2. It should be apparent to one of ordinary skill in the art that the flow chart functions may be configured in a hardwired logic circuit or in software by the use of a microprocessor which carries out the logical functions described in the functional flow chart. The actual configuration of the flow chart logic, either in hardware or in microprocessor-based firmware, would be relatively straightforward to one of ordinary skill.

For example, the acceleration/deceleration detecting system 17 may include any conventional microprocessor having associated random access memory (RAM) and read-only memory (ROM) along with necessary data and address lines. The microprocessor system receives, as an input, the electrical signals reflecting the R-waves from the R-wave detector 9 and provides an output signal to the arrhythmia detector logic circuit 15, or may itself perform the arrhythmia logic functions.

The series of heart beat, or R-wave, signals from the R-wave detector 9 are read by the microprocessor and the heart rate is determined for a group of the series of R-waves, and stored in an appropriate memory location, such as in RAM (decision block 19). Preferably the heart rate is calculated for a group of two successive R-wave signals and then upon receipt of each successive R-wave. (Alternatively, the heart rate may be calculated for a larger number of R-waves signals, e.g., every three heart beats, a new heart rate is calculated.) The instantaneous heart rate is determined by the microprocessor as each successive R-wave is detected and the successive heart rates are stored in memory. Initially, at least four distinct heart rates are calculated (requiring at least five R-waves) and stored in memory.

As the instantaneous heart rates are determined by decision block 19, each beat-to-beat rate ($R_n$) is compared with the prior beat-to-beat rate ($R_{n-1}$) to determine if it exceeds a predetermined value A as depicted in decision block 21. If the beat-to-beat heart rate ($R_n$) exceeds the prior beat-to-beat heart rate ($R_{n-1}$) by a value greater than A, the system continues to decision block 23 in a manner to be described. For example, assume that the value A is 15, representing 15 beats per minute (bpm). If the heart rate ($R_n$) exceeds the prior heart rate ($R_{n-1}$) by 15 bpm, an acceleration is determined and the system continues to decision block 23, to be described. If the increase in heart rate is less than 15 bpm, a negative (No) determination is made and the system returns and keeps checking until the heart rate has increased over the prior heart rate by the predetermined value A.

If an acceleration is determined in decision block 21, and the system continues to decision block 23, the heart rate ($R_n$) is compared with the next succeeding heart rate ($R_{n+1}$) to determine if it exceeds the succeeding heart rate by a value greater than a predetermined value B. If such determination is affirmative (Yes) then a deceleration is determined and the system loops back to the beginning of decision block 21. That is, if an acceleration of the heart rate is immediately followed by a deceleration (a deceleration greater than the value B) an arrhythmic condition is not assumed and the system continues to monitor incoming heart rate. (Such determination indicates a PVC, discussed below.) If such excessive deceleration is not determined (No), the system continues to decision block 25.

Once the value of A is determined, the value for B can be readily chosen depending on the sensitivity desired. For example, once the value for A is selected, one now knows where a premature beat would fall between two "normal" beats. The total time interval over three beats, from a normal beat to a premature beat to the next normal beat, is generally the same as the time interval over three normal beats. That is, at a "normal" rate of 60 bpm, the time interval over three beats is 2000 msec. If the value for A is 15, a PVC would then occur at 787 msec after the first beat (i.e., at 76 bpm), followed by the next beat 1213 msec later (i.e., at 49 bpm). Thus B, in this instance, would be at least equal to 26.

With reference to decision block 25, the system then determine whether the acceleration was immediately preceded by a large deceleration. That is, the immediately preceding heart rate ($R_{n-1}$) is compared with its immediately preceding heart rate ($R_{n-2}$). If the second most preceding heart rate ($R_{n-2}$) exceeds the immediately preceding heart rate ($R_{n-1}$) by a value greater than the predetermined value B, then a large deceleration is assumed. If such occurs, as indicated by the "Yes" output of decision block 25, then an AGC drop-out is assumed and the system loops back to continue to operate on subsequent heart rates. That is, if a large deceleration prior to a large acceleration were detected, no output from the acceleration detector 17 is provided. If a large deceleration is not determined (output "No" of block 25), the system continues to block 27.

Assuming that a large acceleration was detected (from decision block 21) and no large deceleration subsequent to (decision block 23) and prior to (decision block 25) the large acceleration was found, the system provides an output to the arrhythmia detector 15, as depicted by decision block 27. Preferably, the output signal is maintained for a predetermined time period following the satisfaction of the conditions of blocks 21, 23 and 25. That is, if a large acceleration of the heart rate is detected, without the detection of a prior or subsequent large deceleration, an output signal or "true" signal, is provided to the arrhythmia detector 15 and maintained for a predetermined time period. Alternatively, it may be advantageous for the output to be provided to the detector 15 only after a predetermined number of the above-described arrhythmic conditions are satisfied in a given time period, or over a predetermined number of heart beats. That is, the output signal is provided from decision block 27 only if, for example, five acceleration/no deceleration conditions have occurred in a given time period or over a predetermined number of beats.

Figure 3:
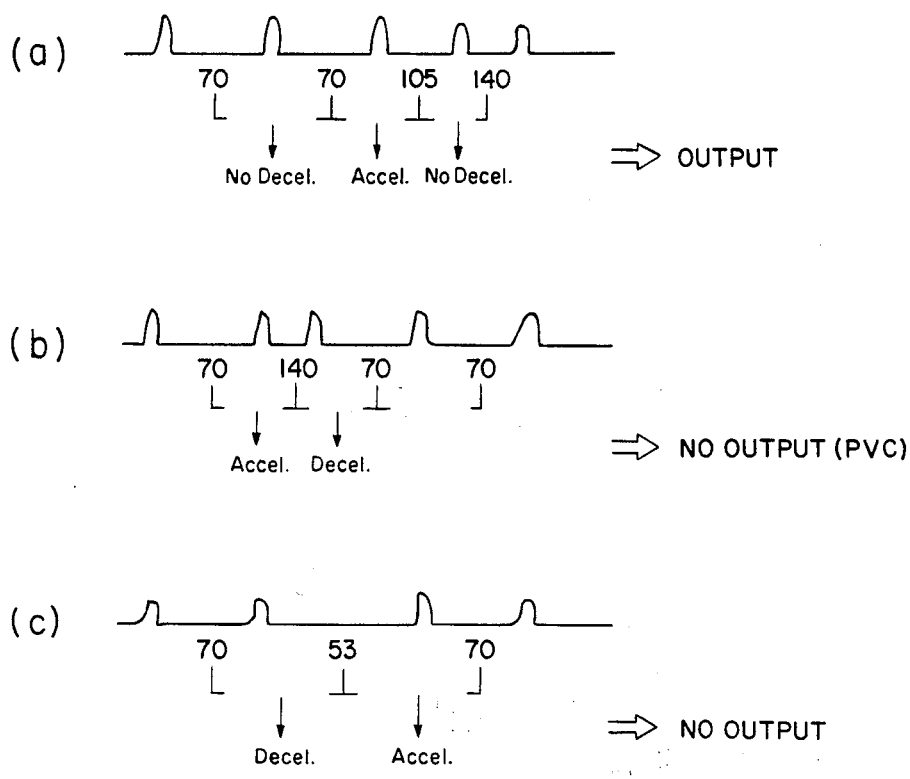
FIG. 3 is a graphical representation of a series of R-waves.

FIG. 3 is a graphical representation of three distinct series of heart beats, representing the output of the R-wave detector 9, to exemplify how the acceleration/deceleration detecting system 17 operates. With reference to waveform (a) of FIG. 3, a heart rate of 70 bpm is determined from the first two R-waves, the next R-wave is detected at 70 bpm, the next R-wave is detected at 105 bpm, followed by an 140 bpm rate. Upon detection of a heart rate change from 70 bpm to 105 bpm, an acceleration signal is determined (decision block 21). The system then checks to see if such acceleration was followed by a large deceleration (decision block 23). Since the rate increased from 105 bpm to 140 bpm, a large deceleration was not detected. (Thus, the output of decision block 23 is No). The system then checks if the acceleration was preceded by a large deceleration (decision block 25). In the example of Waveform (a), the two prior heart rates were constant at 70 bpm and, thus, the output of decision block 25 would be "No", i.e. there was no large deceleration. Thus, an output would be provided to the arrhythmia detector logic circuit 15.

With reference to Waveform (b) of FIG. 3, the waveform depicted shows the heart rate of increasing from 70 bpm to 140 bpm followed by a rate of 70 bpm. Thus, a large acceleration is immediately followed by a large deceleration. This is indicative of a premature ventricular contraction (PVC) and would result in no output provided to the arrhythmia detector logic 15.

With reference to Waveform (c) of FIG. 3 the heart rate declines from 70 bpm to 53 bpm followed by an increase to 70 bpm. Assuming that the increase from 53 bpm to 70 bpm exceeds the acceleration threshold (A), thus making the output of decision block 21 "Yes", the system then checks to see if such acceleration was preceded by a large deceleration. In this case, there was a deceleration from 70 bpm to 53 bpm. Assuming that this difference is greater than the deceleration threshold value (B), the output of decision block 25 would be "Yes", and thus, there would be no output provided to the arrhythmia detector 15. This latter waveform would be typical of an AGC dropout in the R-wave detector circuit 9.

It should be apparent that for those R-wave detecting circuits 9 that do not use an AGC feedback path, so that there is no concern of an AGC dropout, then the decision block 25 may be omitted. That is, a signal would be provided to the arrhythma detector 15 if a large acceleration is detected followed by the absence of a large deceleration, ignoring whether a large deceleration preceded the detection of the large acceleration.

It should be apparent that the above described system is also useful for detecting a PVC condition. As shown in FIG. 1, a PVC output terminal 18 is provided which may be connected with any conventional indicator, such as a visual display. When the logic within the system 17 determines a PVC condition (i.e. when the decision block 23 in FIG. 2 is "Yes"), a signal over terminal 18 is provided to indicate that a PVC was detected.

While preferred forms and arrangements of the invention have been shown and illustrated, it is to be clearly understood that various changes may be made without departing from the spirit and scope of this disclosure. The scope of this invention is to be determined with reference to the accompanying claims.

I claim:

1. An arrhythmia detection system for an automatic defibrillator/cardioverter capable of sensing heart activity and delivering high-energy electrical pulses to the heart in response to an arrhythmia detection, the system comprising:
   ECG input means for receiving an ECG waveform;
   R-wave detecting means operatively connected with said ECG input means for detecting the presence of the R-waves;
   rate averaging means operatively connected with the R-wave detecting means for determining the average R-wave rate and for providing a rate averaging signal when the average R-wave rate exceeds a predetermined value;
   acceleration detector means, operatively connected with said R-wave detecting means, for determining the rate of acceleration of a series of R-waves and for providing a acceleration output signal when the rate of acceleration of the R-waves exceeds a predetermined value;
   arrhythmia detection means operatively connected with said rate averaging means and said acceleration detector means for providing an arrhythmia signal to activate a defibrillator/cardioverter pulse generator in response to receipt of the rate averaging signal and the acceleration output signal.

2. The arrhythmia detection system of claim 1 wherein said acceleration detector means includes means for providing an acceleration output signal when the rate of acceleration of a series of R-waves exceeds a first predetermined value and the rate of deceleration of an immediately succeeding series of R-waves is less than a second predetermined value.

3. The arrhythmia detection system of claim 2 wherein said acceleration detector means includes means for providing an acceleration output signal further when the rate of deceleration of an immediately preceding group of a series of R-waves is less than the second predetermined value.

4. An arrhythmia detection system for an automatic defibrillator/cardioverter capable of sensing heart activity and delivering high-energy electrical pulses to the heart in response to an arrhythmia detection, the system comprising:
   ECG input means for receiving an ECG waveform;
   R-wave detecting means operatively connected with said ECG input means for detecting the presence of R-waves and for providing an R-wave signal upon such detection;
   rate averaging means operatively connected with said R-wave detecting means for receiving a series of R-wave signals, for determining the average R-wave rate, and for providing a rate averaging signal when the average R-wave rate exceeds a predetermined R-wave rate value;
   acceleration detection means operatively connected with said R-wave detecting means for receiving a series of R-wave signals, said acceleration detection means including means for determining at least three successive R-wave rates from the R-wave signals, means for comparing the successive R-wave rates and for providing an acceleration output signal when the second of the successive R-wave rates exceeds the first R-wave rate by a first predetermined value and the second R-wave rate does not exceed the third R-wave rate by a second predetermined value; and
   arrhythmia detection means operatively connected with said rate averaging means and said acceleration detection means for providing an arhythmia signal to activate a defibrillator/cardioverter pulse generator in response to receipt of the rate averaging signal and the acceleration output signal.

5. The arrhythmia detection system of claim 4 wherein said acceleration detection means includes means for determining at least four successive R-wave rates from the R-wave signals, and wherein said means for comparing successive R-wave rates includes means for comparing said first R-wave rate with an immediately prior R-wave rate and for providing the acceleration output signal when the prior R-wave rate does not exceed the first R-wave rate by said second predetermined value.

* * * * *